US005616701A

United States Patent [19]
Woodard et al.

[11] Patent Number: 5,616,701
[45] Date of Patent: Apr. 1, 1997

[54] DNA PURIFICATION BY SOLID PHASE EXTRACTION USING A HYDROXIDE-WASHED GLASS FIBER MEMBRANE

[75] Inventors: Daniel L. Woodard; Adriann J. Howard, both of Raleigh; James A. Down, Cary, all of N.C.

[73] Assignee: Becton Dickinson and Company, Franklin Lakes, N.J.

[21] Appl. No.: 449,441

[22] Filed: May 24, 1995

Related U.S. Application Data

[62] Division of Ser. No. 127,404, Sep. 27, 1993, Pat. No. 5,438,127.
[51] Int. Cl.$^6$ .................................... C07H 21/04
[52] U.S. Cl. ............... 536/25.4; 536/25.41; 536/25.42; 210/500.23; 210/500.26; 210/503; 210/656; 210/658; 501/35; 502/407; 502/408; 502/411
[58] Field of Search ............... 536/25.4, 25.41, 536/25.42; 210/500.23, 500.26, 503, 656, 658; 501/35; 502/407, 408, 411

[56] References Cited

U.S. PATENT DOCUMENTS

| | | | |
|---|---|---|---|
| 4,935,342 | 6/1990 | Seligson et al. | 435/6 |
| 5,234,809 | 8/1993 | Boom et al. | 435/91 |
| 5,438,127 | 8/1995 | Woodard et al. | 536/25.4 |

FOREIGN PATENT DOCUMENTS

| | | |
|---|---|---|
| 0130055 | 1/1985 | European Pat. Off. . |
| 0281390 | 9/1988 | European Pat. Off. . |
| 0512768 | 11/1992 | European Pat. Off. . |
| 0555798 | 8/1993 | European Pat. Off. . |

OTHER PUBLICATIONS

Marko et al., "A Procedure for the Large–Scale Isolation of Highly Purified Plasmid DNA Using Alkaline Extraction and Binding to Glass Powder," *Anal. Biochem.*, 121, 382–387(1982).

Vogelstein et al., "Preparative and Analytical Purification of DNA from Agarose," *Proc. Nat. Acad. Sci USA*, 76(2), 615–619 (1979).

Boom et al.(II), "Rapid and Simple Method for Purification of Nucleic Acids," *J. Clin. Microbiol.*, 28(3), 495–503 (1990).

Willis et al., "Prep–A–Gene™: A Superior Matrix for the Purification of DNA and DNA Fragments," *Biotechniques*, 9(1), 92–99 (1990).

Lutze et al., "A Quick and Efficient Method for the Recovery of Plasmid or Viral DNA from Mammalian Cells," *Nucleic Acids Res.*, 18(20), 6150 (1990).

Chow et al., "Quantitation of DNA Fragmentation Using Fiberglass Filters," *Anal. Biochem.*, 183, 42–45 (1989).

McCormick, "A Solid–Phase Extraction Procedure for DNA Purification," *Anal. Biochem.*, 181, 66–74 (1989).

Upadhyay et al., "Adsorption of Nucleic Acids at the Alumina–Water Interface," *Biochim. Biophys. Acta*, 161, 561–563 (1968).

Walsh et al., "Extended N–Terminal Sequencing of Proteins of Archaebacterial Ribosomes Blotted from Two–Dimentional Gels onto Glass Fiber and Poly(vin=lidene difluoride) Membrane," *Biochemistry*, 27(18), 6867–6876 (1988).

Eckerskorn et al., "A New Siliconized–Glass Fiber as Support for Protein–Chemical Analysis of Electroblotted Proteins," *Eur. J. Biochemistry*, 176, 509–519 (1988).

Snyder et al., *Introduction to Modern Liquid Chromatography*, John Wiley & Sons, New York, 1979, see pp. 272–278.

Birnboim, "A Rapid Alkaline Extraction Method for the Isolation of Plasmid DNA," Ch. 17 in *Methods in Enzymology, vol. 100*, Wu et al. eds., Academic Press, 1983, New York, see pp. 243–255.

Primary Examiner—John Kight
Assistant Examiner—L. Eric Crane
Attorney, Agent, or Firm—David W. Highet, Esq.

[57] ABSTRACT

The present invention relates to modified glass fiber membranes which exhibit sufficient hydrophilicity and sufficient electropositivity to bind DNA from a suspension containing DNA and permit elution of the DNA from the membrane. Generally, the hydrophilic and electropositive characteristics are expressed at the surface of the modified glass fiber membrane. Preferred modified glass fiber membranes of the present invention include glass fiber membranes that have been modified by treatment with trifluoroacetic acid (TFA), $BCl_3$, $SiCl_4$, NaOH, $F^-$, $AlCl_3$ alone or in combination, with or without water. The modified glass fiber membranes of the present invention are particularly useful in processes for purification of DNA from other cellular components. In these processes, a suspension of cellular components is placed in contact with the modified glass fiber membrane, the modified glass fiber membrane is washed to remove all cellular components other than DNA which are bound to the membrane, and the bound DNA is eluted from the membrane.

1 Claim, No Drawings

DNA PURIFICATION BY SOLID PHASE EXTRACTION USING A HYDROXIDE-WASHED GLASS FIBER MEMBRANE

This is a division of application Ser. No. 08/127,404, filed Sep. 27, 1993, now U.S. Pat. No. 5,438,121.

BACKGROUND OF THE INVENTION

The present invention relates generally to the purification of DNA by solid phase extraction, and more specifically to modified glass fiber membranes which are capable of binding DNA and eluting DNA under suitable conditions.

The preparation of high-purity double-stranded (ds) plasmid DNA, single-stranded (ss) phage DNA, chromosomal DNA and agarose gel-purified DNA fragments is of critical importance in molecular biology. Ideally, a method for purifying DNA should be simple, rapid and require little, if any, additional sample manipulation. DNA rendered by such a method should be immediately amenable to transformation, restriction analysis, ligation or sequencing. A method with all of these features would be extremely attractive in the automation of DNA sample preparation, a goal of research and diagnostic laboratories. Typically, the preparation of plasmid DNA from crude alcohol precipitates is laborious, most often utilizing CsCl gradients, gel filtration, ion exchange chromatography, or Rnase, proteinase K and repeated alcohol precipitation steps. These methods also require considerable downstream sample preparation to remove CsCl and other salts, ethidium bromide and alcohol. Similar arguments extend when using any of these methods for purifying DNA fragments. A further problem with these methods is that small, negatively-charged cellular components can co-purify with the DNA. Thus, the DNA can have an undesirable level of contamination.

DNA can also be purified using solid phases. Conventional solid phase extraction techniques have utilized surfaces which either (1) fail to attract and hold sufficient quantities of DNA molecules because of surface design to permit easy recovery of the DNA molecules during elution, or (2) excessively adhere DNA molecules to the surface, thereby hindering recovery of the DNA molecules during elution. Conventional surface materials which cause these problems when utilized in solid phase extraction include silica surfaces such as glass and Celite. Adequate binding of DNA to these types of surfaces can be achieved only by utilizing high concentrations of chaotropes or alcohols which are generally toxic, caustic, and/or expensive. For example, it is known that DNA will bind to crushed glass powders and to glass fiber filters in the presence of chaotropes. The chaotropic ions typically are washed away with alcohol, and the DNAs are eluted with low-salt solutions or water. Importantly, RNA and protein do not bind. However, a serious drawback in the use of crushed glass powder is that its binding capacity is low. In addition, glass powders often suffer from inconsistent recovery, incompatibility with borate buffers and a tendency to nick large DNAs. Similarly, glass fiber filters provide a nonporous surface with low DNA binding capacity. Other silicas, such as silica gel and glass beads, are not suitable for DNA binding and recovery. Currently, the solid phase of choice for solid phase extraction of DNA is Celite such as found in Prep-A-Gene™ by Bio-Rad Laboratories. As with the crushed glass powders, high concentrations of chaotropes are required for adequate binding of the DNA to the Celite.

SUMMARY OF THE INVENTION

These problems with conventional DNA purification methods are addressed by the present invention, which relates to modified glass fiber membranes which exhibit sufficient hydrophilicity and sufficient electropositivity to bind DNA from a suspension containing DNA and permit elution of the DNA from the material. Generally, the hydrophilic and electropositive characteristics are expressed at the surface of the modified glass fiber membrane, and are quantified as the presence of oxygen as measured by Fourier transform infrared spectroscopy (FTIR) and the presence of the substituted atom as detected by electron surface composition analysis (ESCA). Preferred modified glass fiber membranes of the present invention include glass fiber membranes that have been modified by treatment with trifluoroacetic acid (TFA), $BCl_3$, $SiCl_4$, NaOH, $F^-$, $AlCl_3$ alone or in combination, and further with or without treatment with water.

The modified glass fiber membranes of the present invention are particularly useful in processes for purification of DNA from other cellular components. In these processes, a suspension of cellular components is placed in contact with the modified glass fiber membrane, the modified glass fiber membrane is washed to remove all cellular components other than DNA which are bound to the membrane, and the bound DNA is eluted from the membrane.

DETAILED DESCRIPTION OF THE INVENTION

The present invention relates to a modified glass fiber membrane which exhibits sufficient hydrophilicity and sufficient electropositivity to bind DNA from a suspension of cellular components and permit elution of the DNA from the membrane. It has been found that much lower concentrations of chaotropes or alcohols can be utilized to achieve purification of DNA using the instant modified glass fiber membranes. Binding of DNA to the modified glass fiber membranes allows the use of such membranes for automated DNA isolation processes and for sample processing steps for DNA probe tests. For example, using a dot-blot apparatus, 96 samples can be done at once, and rapidly.

DNA interacts with a solid phase surface in two ways. First, DNA interacts with the surface through hydrogen bonding between hydroxyl groups of DNA and surface components of the solid phase, such as surface hydroxyls. The second interaction is between the negatively charged phosphates of the DNA and positively charged elements of the solid phase surface. The hydrophilic and electropositive characteristics of the solid phase surface must be such as to allow binding of the DNA from a suspension of cellular components, a suspension of nucleic acids and other materials and/or a suspension of nucleic acids, and to permit elution of the DNA from the solid phase material. Thus, the electropositive characteristics of the solid phase material cannot have too high of a positive charge, or the DNA will stick to the surface and cannot be eluted. This characteristic is also true for many metal-based surfaces, which has resulted in their inability to be utilized for purification of DNA.

Silicon-containing materials, e.g., silica, Celite, glass powders and the like, have been used for DNA purification with mixed results. Some of these surfaces have low binding capacities and/or require the use of highly concentrated solutions of chaotropes or alcohols for the binding of DNA. Thus, it is desired to produce solid phase surfaces, particularly solid phases of modified glass fiber membranes, which exhibit suitable hydrophilic and electropositive characteristics for DNA purification and/or for DNA purification with much lower concentrations of chaotropes or alcohols. On the surface of the solid phase, hydrophilic characteristics are achieved by the presence of groups that will attract water molecules. Suitable groups include —OH, —NH, —F, —H or groups with double-bonded oxygen such as carbonyl, sulfonyl or phosphonyl. Electropositive characteristics are achieved by the presence of positively charged atoms. Suitable positively-charged atoms include Si, B or Al. In accordance with the present invention, modified glass fiber membranes are prepared in which the hydrophilic characteristics are achieved by incorporation of the appropriate hydrophilic groups, and the electropositive characteristics are achieved by incorporation of Si and other appropriate positively-charged atoms. Preferred modified glass fiber membranes of the present invention include glass fiber membranes that have been modified by treatment with trifluoroacetic acid (TFA), $Bcl_3$, $SiCl_4$, NaOH, $F^-$, $AlCl_3$, alone or in combination, and further with or without treatment with water.

In general, the modified glass fiber membranes of the present invention are prepared by treating a glass fiber membrane with either TFA or 0.2N NaOH overnight at 15° C. to 30° C., preferably at 20° C. to 25° C., and most preferably at room temperature. The TFA- or NaOH-treated glass fiber membranes could be used directly or could be further treated with NaOH, $Bcl_3$, $SiCl_4$, $AlCl_3$ or $F^-$, and if desired, further treated with 0.2N NaOH or $H_2O$. These latter treatments were generally conducted as previously described except the treatment with $AlCl_3$ and $SiCl_4$ was most preferably at 22° C. to 35° C. Several of the modified glass fiber membranes gave superior performance (i.e., a greater recovery of DNA) when compared to the unmodified surfaces, and others provided the same recovery of DNA. Glass fiber membranes which were modified such that undesired hydrophilicity and/or electropositivity resulted, provided no recovery of DNA.

Glass fiber membranes, such as Whatman G/F B or C membranes, treated with the following materials, provided recovery of DNA:

TFA

TFA, $BCl_3$ and $H_2O$

NaOH, $SiCl_4$ and NaOH

NaOH, $BCl_3$ and $H_2O$

NaOH, $PCl_3$ and $H_2O$

NaOH

TFA and NaOH

TFA and $F^-$

TFA and $BCl_3$

NaOH, $BCl_3$ and NaOH

NaOH, $AlCl_3$ and NaOH

Glass fiber membranes, such as Whatman G/F B or C membranes, treated with the following materials, provided DO recovery of DNA:

TFA, $AlCl_3$ and $H_2O$

TFA, $SiCl_4$ and $H_2O$

TFA and $SiCl_4$

TFA and $AlCl_3$

NaOH, $AlCl_3$ and $H_2O$

NaOH, $SiCl_4$ and $H_2O$

The modified glass fiber membranes of the present invention are used for the purification of DNA from other cellular components or potential contaminants. The DNA can be obtained from any source, including but not limited to crude cell extracts, biological fluids, phage supernatants, agarose gels and radiolabelling reactions. The DNA can be double-stranded, single-stranded, circular or linear, and can be variable in size. Conventional techniques for obtaining DNA from any source, well known in the art, are utilized to prepare the DNA for purification. Typical procedures for obtaining DNA end with a suspension of the DNA in solution. For isolation of DNA from biological samples, see, e.g., Harding, J. D. et al., *Nucleic Acids Research* 17:6947 (1989) and Marko, M. A. et al., *Analytical Biochemistry* 121:382 (1982). Procedures for isolation of plasmid DNA can be found in Lutze, L. H. et al., *Nucleic Acids Research* 20:6150 (1990). Extraction of double-stranded DNA from biological samples can be found in Yamada, O. et al., *Journal of Virological Methods* 27:203 (1990). Most DNA solutions comprise the DNA in a suitable buffer such as TE (Tris-EDTA), TEA (40 mm Tris-acetate, 1 mm EDTA) buffer, or a lysate. See also Sambrook, J. et al., *Molecular Cloning: A Laboratory Manual,* 2nd Ed., Cold Spring Harbor Laboratory Press, New York (1989).

Once the DNA is obtained in a suitable solution or suspension, the modified glass fiber membrane of the present invention is added to the solution or suspension. Alternatively, the DNA solution or suspension could be added to the modified glass fiber membrane of the present invention using a dot blot apparatus that pulls the suspension through the filter. After the DNA solution or suspension is contacted with the modified glass fiber membrane of the present invention, a binding buffer typically is added to assist in the binding of the DNA to the membrane. Suitable binding buffers include well-known chaotropes such as $NaClO_4$ and NaI, and other agents such as guanidine Hcl, NaCl or isopropanol. After the DNA is bound to the modified glass fiber membrane, the pure DNA is eluted from the membrane. Suitable eluting agents include 10 mM Tris, Ph 7.0 or water. Generally, the modified glass fiber membrane with bound DNA is washed prior to eluting the DNA. Suitable washing agents include 80/20 ethanol/50 mM Tris, Ph 7.0 and other low molecular wight alcohols.

The DNA obtained by purification with the modified glass fiber membranes of the present invention may be used without further manipulation for restriction enzyme digestion, cloning, sequencing, diagnostics and the like. The high quality of DNA prepared with the present invention and the speed with which DNA is purified, with minimal downstream processing, mean that these modified glass fiber membranes can be useful in the automation of DNA sample preparation.

The modified glass fiber membranes of the present invention allow very quick and efficient isolation of DNA from biological samples. They can substantially decrease the time required to process pure DNA from biological samples, compared with currently used techniques, and in some cases generate high quantities of pure DNA. With these advantages, the modified glass fiber membranes are useful for part of the sample processing step in DNA probe tests. One example is use of the modified glass fiber membranes in a dot blot apparatus which allows the rapid processing of 96 samples at one time.

The present invention is described by reference to the following Examples, which are offered by way of illustration and are not intended to limit the invention in any manner. Standard techniques well known in the art or the techniques specifically described below were utilized.

EXAMPLE 1

Synthesis of Modified Glass Fiber Membranes

A. Treatment with TFA

Glass fiber membranes, Whatman G/F B or C, were treated with TFA (Aldrich Chemical Co.) by adding 20 ml of TFA to a 50 ml beaker. The membranes were added to the beaker one at a time. The beaker with TFA and the membranes was allowed to stand overnight at room temperature. The TFA-treated membranes were then placed in a desiccator, attached to an aspirator with a KOH trap and stored under reduced pressure overnight to remove TFA.

B. Treatment with NaOH

Glass fiber membranes, Whatman G/F B or C, were treated with 0.2N NaOH by adding 20 ml of NaOH to a 50 ml beaker. The membranes were added to the beaker one at a time. The beaker with NaOH and the membranes was heated on low (35° C.) for two hours, and then allowed to stand overnight at room temperature. The NaOH-treated membranes were washed four times with 20 ml water and three times with 20 ml acetone. The NaOH-treated membranes were air-dried for 20 minutes, oven-dried one hour at 100° C., and stored in a desiccator.

TFA-treated glass fiber membranes prepared as described above were also treated with 0.2N NaOH, as described above, except that the TFA-treated membranes were added to 40 ml NaOH and heated on low (35° C.) overnight.

$SiCl_4$-, $BCl_3$- or $AlCl_3$-treated—NaOH treated glass fiber membranes prepared as described below were treated with 0.2N NaOH to replace chlorine groups with hydroxyl groups, by adding 40 ml of NaOH to a 100 ml beaker. The membranes were added to each beaker and heated on low (35° C.) overnight. The NaOH-treated membranes were filtered, placed in a fritted funnel, washed three times with 2 ml water and three times with 2 ml acetone, air-dried for 15 minutes, and oven-dried for one hour at 35° C. The NaOH-treated $SiCl_4$-treated-NaOH-treated (hereinafter NaOH/$SiCl_4$/NaOH-treated) glass fiber membranes, the NaOH-treated $BCl_3$-treated-NaOH-treated (hereinafter NaOH/$BCl_3$/NaOH-treated) glass fiber membranes, and the NaOH-treated $AlCl_3$-treated-NaOH-treated (hereinafter NaOH/$AlCl_3$/NaOH-treated) glass fiber membranes were stored in a desiccator.

C. Treatment with Fluoride

TFA-treated glass fiber membranes prepared as described above were treated with fluorine by adding (a) 5 ml of tetrabutylammonium fluoride (TBAF) and 5 ml tetrahydrofuran (THF) (5 mM), or (b) 10 ml TBAF (10 Mm) to 50 ml beakers. TFA-treated glass fiber membranes were added to each beaker and heated on low (35° C.) overnight. The fluoride-treated membranes were put in a fritted funnel and washed repeatedly with water and then with acetone, air-dried ~30 minutes, and oven-dried at 35° C. for one hour. The $F^-$-treated-TFA-treated (hereinafter TFA/$F^-$-treated) glass fiber membranes were stored in a desiccator.

D. Treatment with $SiCl_4$, $BCl_3$, $AlCl_3$ or $PCl_3$

TFA-treated glass fiber membranes prepared as described above were treated with $SiCl_4$, $BCl_3$ or $AlCl_3$ by adding (a) 10 ml of $BCl_3$ (1M in $CH_2$; Aldrich Chemical Co.) and 5 ml of THF; (b) 10 ml of $AlCl_3$ (1M in nitrobenzene; Aldrich Chemical Co.), or (c) 20 ml $SiCl_4$ (Petrach Systems) to 50 ml beakers. TFA-treated glass fiber membranes were added to each beaker and heated on low (35° C.) overnight. The $SiCl_4$-, $BCl_3$- or $AlCl_3$-treated membranes were washed repeatedly with acetone, air-dried ~30 minutes, and oven-dried one hour at 35° C. The $SiCl_4$-treated-TFA-treated (hereinafter TFA/$SiCl_4$-treated) glass fiber membranes, $AlCl_3$-treated-TFA-treated (hereinafter TFA/$AlCl_3$-treated) glass fiber membranes, and $BCl_3$-treated-TFA-treated (hereinafter TFA/$BCl_3$-treated) glass fiber membranes were stored in a desiccator.

NaOH-treated glass fiber membranes prepared as described above were treated with $SiCl_4$, $BCl_3$, $AlCl_3$ or $PCl_3$ by adding (a) 20 ml $SiCl_4$ (Pettach Systems); (b) 20 ml $BCl_3$ (1N in $CH_2Cl_2$; Aldrich Chemical Co.); (c) 20 ml $AlCl_3$ (1M in nitrobenzene; Aldrich Chemical Co.); or (d) 20 ml $PCl_3$ (2M in $CH_2Cl_2$; Aldrich Chemical Co.) to a 100 ml beaker. NaOH-treated glass fiber membranes were added to each beaker. Beakers containing the membranes and $BCl_3$, $AlCl_3$ or $SiCl_4$ were heated on low (35° C.) overnight. The beakers containing the membranes and $BCl_3$ or $PCl_3$ were allowed to stand overnight at room temperature. The $SiCl_4$-, $BCl_3$-, $AlCl_3$- or $PCl_3$-treated membranes were washed alternatively either (a) three times with 10 ml water and three times with 10 ml acetone, or (b) three times with 10 ml acetone, three times with 10 ml water and three times with 10 ml acetone, air-dried and then oven-dried one hour at 35° C. The $SiCl_4$-treated-NaOH-treated (hereinafter NaOH/$SiCl_4$-treated) glass fiber membranes, $BCl_3$-treated-NaOH-treated (hereinafter NaOH/$BCl_3$-treated) glass fiber membranes, and $AlCl_3$treated-NaOH-treated (hereinafter NaOH/$AlCl_3$-treated) glass fiber membranes were stored in a desiccator.

E. Treatment with Water

The TFA/$SiCl_4$-, TFA/$BCl_3$-, TFA/$AlCl_3$-, NaOH/$SiCl_4$-, NaOH/$BCl_3$-, NaOH/$AlCl_3$- or NaOH/$PCl_3$-treated glass fiber membranes prepared as described above were treated with water to replace chlorine groups with hydroxyl groups, by adding 20 ml of water to a 50 ml beaker. The modified glass fiber membranes were added to separate beakers and heated on low (35° C.) overnight for the TFA-treated class or stored overnight at room temperature for the NaOH-treated class. The TFA-treated class were then placed in a fritted funnel and washed three times with 15 ml acetone, air-dried for 15 minutes, and oven-dried one hour at 35° C. The NaOH-treated class were washed three times with 10 ml water. The $H_2O$-treated-TFA/$SiCl_4$-treated (hereinafter TFA/$SiCl_4$/$H_2O$-treated) glass fiber membranes, the $H_2O$-treated-TFA/$Bcl_3$-treated (hereinafter TFA/$Bcl_3$/$H_2O$-treated) glass fiber membranes, the $H_2O$-treated-TFA/$AlCl_3$-treated (hereinafter TFA/$AlCl_3$/$H_2O$-treated) glass fiber membranes, the $H_2O$-treated-NaOH/$SiCl_4$-treated (hereinafter NaOH/$SiCl_4$/$H_2O$-treated) glass fiber membranes, the $H_2O$-treated-NaOH/$Bcl_3$-treated (hereinafter NaOH/$BCl_3$/$H_2O$-treated) glass fiber membranes, the $H_2O$-treated-NaOH/$AlCl_3$-treated (hereinafter NaOH/$AlCl_3$/$H_2O$-treated) glass fiber membranes, and the $H_2O$-treated-NaOH/$PCl_3$-treated (hereinafter NaOH/$PCl_3$/$H_2O$-treated) glass fiber membranes were stored in a desiccator.

EXAMPLE 2

Analysis of DNA Recovery Using Modified Glass Fiber Membranes

A Bio-Rad Bio-Dot apparatus was used to test the membranes. A small strip of each membrane of the following membranes was cut large enough to cover one well or two wells of the apparatus:

| Membrane Number | Whatman G/F Glass Fiber Membrane | Modification |
| --- | --- | --- |
| 1. | B | NaOH |
| 2 | C | TFA |
| 3 | C | TFA/NaOH |
| 4 | C | TFA/F⁻ (5 mM) |
| 5 | C | TFA/F⁻ (10 mM) |
| 6 | C | TFA/AlCl$_3$/H$_2$O |
| 7 | C | TFA/SiCl$_4$/H$_2$O |
| 8 | C | TFA/BCl$_3$/H$_2$O |
| 9 | C | TFA/BCl$_3$ |
| 10 | C | TFA/SiCl$_4$ |
| 11 | C | TFA/AlCl$_3$ |
| 12 | C | NaOH/SiCl$_4$/NaOH |
| 13 | C | NaOH/BCl$_3$/NaOH |
| 14 | C | NaOH/AlCl$_3$/NaOH |
| 15 | B | NaOH/AlCl$_3$/H$_2$O |
| 16 | B | NaOH/BCl$_3$/H$_2$O |
| 17 | B | NaOH/PCl$_3$/H$_2$O |
| 18 | B | NaOH/SiCl$_4$/H$_2$O |

(untreated membranes were used as controls)

After the membranes were properly aligned within the box and it was clamped tightly, the unused wells were covered with tape to maintain vacuum pressure.

Each well was provided with 0.7 ml 6M NaCl$_4$ and 0.78 μg λ DNA (BRL Catalog No. 56125A). Water aspiration was used to apply gentle vacuum to avoid breakage of membranes. After the DNA/chaotrope solution was pulled through, the membranes were washed twice with 350 μl 80% ethanol/50 μM TRIS, pH 7.0. Membranes 7, 10 and 18 did not allow flow-through of DNA chaotrope solution, which was then manually suctioned off prior to washing. The membranes were then removed from the apparatus and trimmed to the shape of the well (which is imprinted on the fitter) and placed in a 0.65 ml microcentrifuge tube. Thirty-five μl of elution buffer (TE=10 mM Tris, 1 mM EDTA, pH 8.0) was added to each tube and incubated for 10 minutes at 40° C. The samples were then spun for about three minutes. Twenty μl of buffer was placed in another tube and about 1 μl Type II Loading Dye (25% Ficoll, 0.25% Bromophenol Blue, 0.25% xylene glycol) was added. Gel electrophoresis was performed on 1% agarose, 1X TAE gel for 25 minutes at 130 volts. The gels were stained in ethidium bromide in water (1:100 dilution of 10 mg/ml stock) for 10 minutes and destained for 15 minutes. Photographs were taken over UV light with Type 57 Polaroid film.

Membranes 2, 8, 12, 16 and 17 recovered DNA better than all of the other membranes, including the unmodified membrane controls. Membrane 17 appeared to recover close to 100% of the DNA. Membranes 1, 3, 4, 5, 9, 13 and 14 recovered DNA apparently about the same as the unmodified controls. Membranes 6, 7, 10, 11, 15 and 18 did not provide any recovery of DNA.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. A method for purifying DNA comprising the steps of:
   (a) contacting a suspension containing DNA with a glass fiber membrane which has been modified by treatment with NaOH, under conditions suitable to bind DNA to said membrane; p1 (b) washing said membrane having bound DNA; and
   (c) eluting the DNA from said membrane.

* * * * *